US012412326B2

(12) United States Patent
Taoka et al.

(10) Patent No.: US 12,412,326 B2
(45) Date of Patent: Sep. 9, 2025

(54) IMAGE PROCESSING APPARATUS AND NON-TRANSITORY COMPUTER READABLE MEDIUM FOR VISUALIZING MAGNETIC RESONANCE DATA

(71) Applicants: National University Corporation Tokai National Higher Education and Research System, Nagoya (JP); CANON MEDICAL SYSTEMS CORPORATION, Tochigi (JP)

(72) Inventors: Toshiaki Taoka, Nagoya (JP); Nobuyasu Ichinose, Otawara (JP); Takaya Mori, Nasushiobara (JP)

(73) Assignees: National University Corporation Tokai National Higher Education and Research System, Nagoya (JP); CANON MEDICAL SYSTEMS CORPORATION, Tochigi (JP)

(*) Notice: Subject to any disclaimer, the term of this patent is extended or adjusted under 35 U.S.C. 154(b) by 164 days.

(21) Appl. No.: 18/052,362

(22) Filed: Nov. 3, 2022

(65) Prior Publication Data
US 2023/0143966 A1 May 11, 2023

(30) Foreign Application Priority Data

Nov. 8, 2021 (JP) .................. 2021-181837

(51) Int. Cl.
G06T 11/20 (2006.01)
A61B 6/00 (2024.01)
(52) U.S. Cl.
CPC .......... G06T 11/206 (2013.01); A61B 6/5217 (2013.01); G06T 2210/41 (2013.01)

(58) Field of Classification Search
CPC ......... G06T 11/206; G06T 2207/10088; G06T 2207/10092; G06T 2207/10096; A61B 5/055
See application file for complete search history.

(56) References Cited

U.S. PATENT DOCUMENTS 6,356,646 B1 * 3/2002 Spencer .................... G06T 7/11
382/103
2009/0143676 A1 6/2009 Matsumura
(Continued)

FOREIGN PATENT DOCUMENTS

JP 3869056 B2 1/2007
JP 5303147 B2 10/2013
(Continued)

OTHER PUBLICATIONS

Wu, Dan, and Jiangyang Zhang. "The effect of microcirculatory flow on oscillating gradient diffusion MRI and diffusion encoding with dual-frequency orthogonal gradients (DEFOG)." Magnetic resonance in medicine 77.4 (2017): 1583-1592. (Year: 2017).*

(Continued)

Primary Examiner — Ryan McCulley
(74) Attorney, Agent, or Firm — Oblon, McClelland, Maier &Neustadt, L.L.P.

(57) ABSTRACT

An image processing apparatus according to an embodiment includes a processing circuitry. The processing circuitry acquires pixel values of at least three different types of magnetic resonance (MR) images. The processing circuitry causes a display to display a diagram in which values based on the pixel values are arranged in a region with at least three-dimensional axes.

19 Claims, 8 Drawing Sheets

(56) References Cited

U.S. PATENT DOCUMENTS

2012/0172700 A1* 7/2012 Krishnan ............... A61B 6/505
                                                    600/407
2017/0071496 A1* 3/2017 Gillies ................. A61B 5/7264
2020/0022616 A1* 1/2020 Bier ....................... A61B 5/055

FOREIGN PATENT DOCUMENTS

JP          5942099 B2    6/2016
WO    WO 2017/134830 A1   8/2017

OTHER PUBLICATIONS

Taoka, "Advanced MR Technology to Improve Imaging Value in Clinical Practice", Department of Innovative Biomedical Visualization (IBMV), Graduate School of Medicine, Nagoya University, 2021 ISMRM & SMRT Annual Meeting & Exhibition, 2021, pp. 1-46.

Office Action issued Jul. 16, 2025, in corresponding Japanese Patent Application No. 2021-181837, 4 pages.

Wasim Khan et al., "Three-tissue compositional analysis reveals in-vivo microstructural heterogeneity of white matter hyperintensities following stroke", NeuroImage, Sep. 2020, vol. 218, p. 116869, DOI: 10.1016/j.neuroimage.2020.116869.

\* cited by examiner

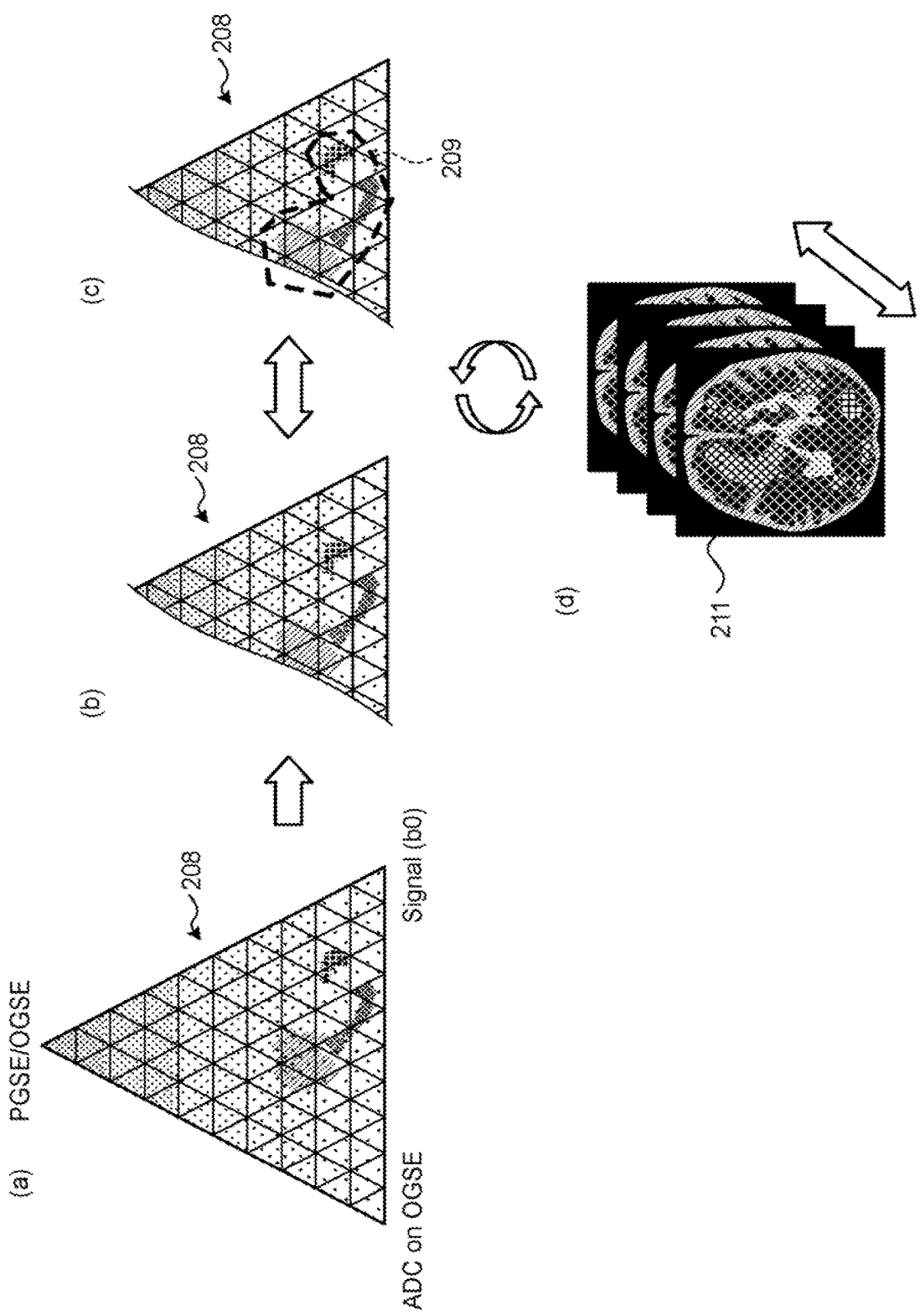

IMAGE PROCESSING APPARATUS AND NON-TRANSITORY COMPUTER READABLE MEDIUM FOR VISUALIZING MAGNETIC RESONANCE DATA

CROSS-REFERENCE TO RELATED APPLICATIONS

This application is based upon and claims the benefit of priority from Japanese Patent Application No. 2021-181837, filed on Nov. 8, 2021; the entire contents of which are incorporated herein by reference.

FIELD

Embodiments described herein relate generally to an image processing apparatus and a non-transitory computer readable medium.

BACKGROUND

In the related art, in the medical field, various diseases are diagnosed using medical images such as magnetic resonance (MR) images taken by a magnetic resonance imaging (MRI) apparatus.

In general, diagnosis using MR images is performed by taking various types of MR images. In such a case, a radiologist interprets characteristics of pathological conditions and extent of progression while constructing, in his/her mind, information obtained from a plurality of types of taken MR images and analysis data. Such interpretation process is subjectively accumulated by each individual.

However, some pathological conditions require expertise in interpretation, since contrast may be similar among a plurality of types of MR images or the contrast itself may be weak even after contrast enhancement. When there are many such pathological conditions, a possibility of misdiagnosis or oversight may be increased. In a case where it is difficult to make a decision, additional imaging may be required, which may extend the examination time or increase a burden on a subject. Such problems may also occur in medical images taken by modalities other than the MRI apparatus.

BRIEF DESCRIPTION OF THE DRAWINGS

FIG. 8 is a diagram illustrating an example of a processing result of processing performed by each processing function of the processing circuitry according to a second embodiment.

DETAILED DESCRIPTION

An image processing apparatus according to embodiments includes an acquisition unit and a display control unit. The acquisition unit acquires pixel values of at least three different types of magnetic resonance (MR) images. The display control unit causes a display to display a diagram in which values based on the pixel values are arranged in a region with at least three-dimensional axes.

Hereinafter, embodiments of an image processing apparatus and a non-transitory computer readable medium are described in detail with reference to the drawings.

First Embodiment

Figure 1:
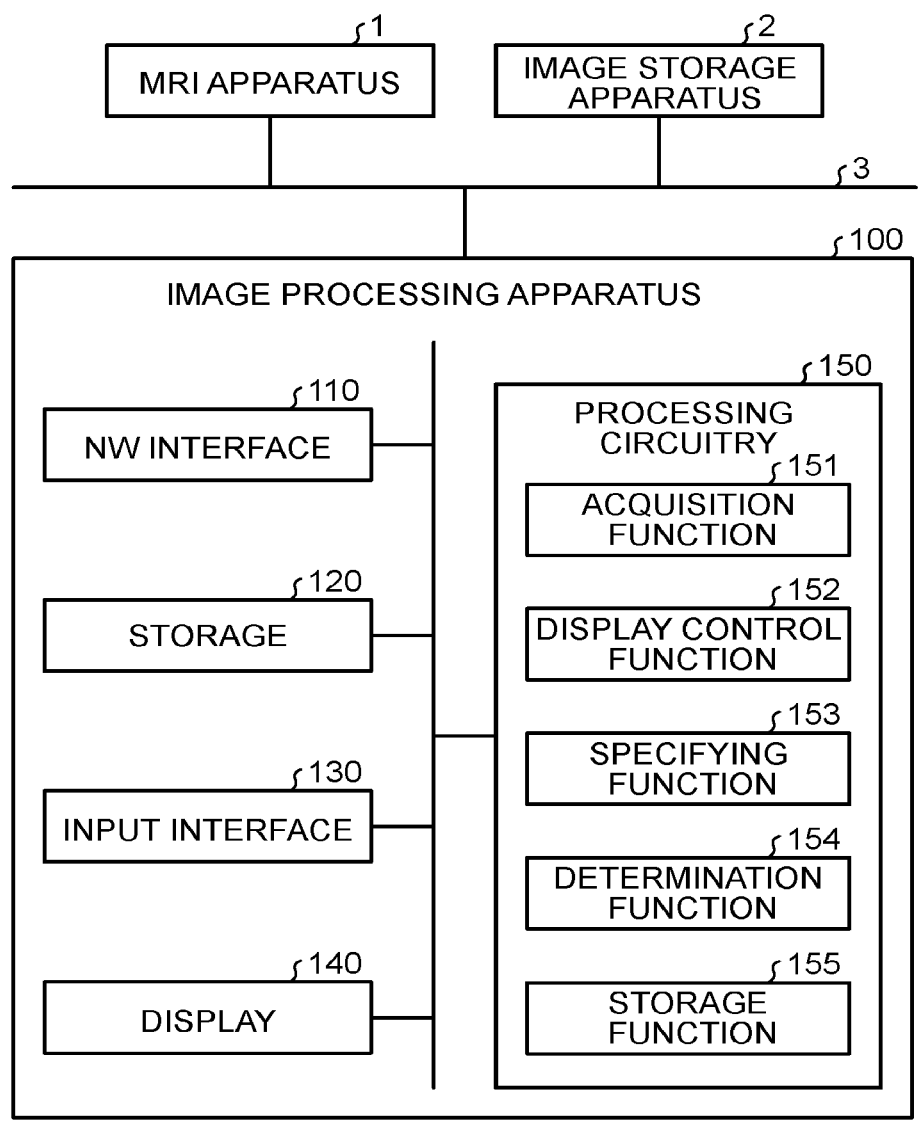
FIG. 1 is a diagram illustrating a configuration example of an image processing apparatus according to a first embodiment.

FIG. 1 is a diagram illustrating a configuration example of an image processing apparatus according to a first embodiment.

For example, as illustrated in FIG. 1, an image processing apparatus 100 according to the present embodiment is connected to an MRI apparatus 1 and an image storage apparatus 2 via a network 3 to be able to communicate with each other. The image processing apparatus 100 may be further connected to other devices (not illustrated) via the network 3.

The MRI apparatus 1 takes an image of a subject by using a magnetic resonance phenomenon. Specifically, the MRI apparatus 1 collects magnetic resonance data from the subject by executing various imaging sequences on the basis of imaging conditions set by an operator. Then, the MRI apparatus 1 generates two-dimensional or three-dimensional MR images by performing image processing such as Fourier transform processing on the collected magnetic resonance data.

The image storage apparatus 2 stores the MR images collected by the MRI apparatus 1. For example, the image storage apparatus 2 is implemented by a computer device such as a picture archiving and communication system (PACS) server, and stores the MR images in a digital imaging and communications in medicine (DICOM)-compliant format.

The image processing apparatus 100 processes the MR images related to the subject. Specifically, the image processing apparatus 100 acquires the MR images from the MRI apparatus 1 or the image storage apparatus 2 via the network 3, and processes the acquired MR images. For example, the image processing apparatus 100 is implemented by a computer device such as a workstation.

For example, the image processing apparatus 100 includes a network (NW) interface 110, storage 120, an input interface 130, a display 140, and processing circuitry 150.

The NW interface 110 controls transmission and communication of various data between the image processing apparatus 100 and other devices via the network 3. Specifically, the NW interface 110 is connected to the processing circuitry 150, and transmits data received from other devices to the processing circuitry 150 and transmits data received from the processing circuitry 150 to other devices. For example, the NW interface 110 is implemented by a network card, a network adapter, a network interface controller (NIC), or the like.

The storage 120 stores various data and various computer programs. Specifically, the storage 120 is connected to the processing circuitry 150, stores data received from the processing circuitry 150, reads the data stored therein, and transmits the read data to the processing circuitry 150. For example, the storage 120 is implemented by a semiconductor memory element such as a random access memory (RAM) and a flash memory, a hard disk, an optical disc, or the like.

The input interface 130 receives input operations of various instructions and various information from the operator. Specifically, the input interface 130 is connected to the processing circuitry 150, converts the input operations received from the operator into electrical signals, and transmits the electrical signals to the processing circuitry 150. For example, the input interface 130 is implemented by a trackball, a switch button, a mouse, a keyboard, a touch pad for performing an input operation by touching an operation surface, a touch screen with integrated display screen and touch pad, a non-contact input interface using an optical sensor, a voice input interface, or the like. In this specification, the input interface 130 is not limited to only those with physical operating components such as a mouse and a keyboard. For example, an example of the input interface 130 also includes electrical signal processing circuitry that receives electrical signals corresponding to input operations from an external input device provided separately from the apparatus and outputs the electrical signals to control circuitry.

The display 140 displays various information and various data. Specifically, the display 140 is connected to the processing circuitry 150 and displays various information and various data received from the processing circuitry 150. For example, the display 140 is implemented by a liquid crystal monitor, a cathode ray tube (CRT) monitor, a touch panel, or the like.

The processing circuitry 150 performs various types of processing by controlling each component included in the image processing apparatus 100. For example, the processing circuitry 150 performs various types of processing according to the input operations received from the operator via the input interface 130. For example, the processing circuitry 150 causes the storage 120 to store data received from other devices via the NW interface 110. For example, the processing circuitry 150 transmits data read from the storage 120 to the NW interface 110, thereby transmitting the data to other devices. For example, the processing circuitry 150 causes the display 140 to display the data read from the storage 120.

The above is the configuration of the image processing apparatus 100 according to the present embodiment. With such a configuration, the image processing apparatus 100 according to the present embodiment has a function of performing an analysis process for supporting diagnosis using MR images.

In general, diagnosis using MR images is performed by taking various types of MR images. In such a case, a radiologist interprets characteristics of pathological conditions and extent of progression while constructing, in his/her mind, information obtained from a plurality of types of taken MR images and analysis data. Such interpretation process is subjectively accumulated by each individual.

However, some pathological conditions require expertise in interpretation, since contrast may be similar among a plurality of types of MR images or the contrast itself may be weak even after contrast enhancement. When there are many such pathological conditions, a possibility of misdiagnosis or oversight may be increased. In a case where it is difficult to make a decision, additional imaging may be required, which may extend the examination time or increase a burden on a subject.

On the other hand, a method called Radiomics is also being studied, in which a large number of feature values of specific lesions are obtained from a plurality of types of MR images and used for diagnosis, but the procedure for extracting and selecting effective feature values is complicated. Furthermore, this method lacks versatility, making it difficult for the unskilled to use.

For this reason, the image processing apparatus 100 according to the present embodiment is configured to be able to facilitate diagnosis using MR images.

Specifically, the image processing apparatus 100 includes an acquisition function 151, a display control function 152, a specifying function 153, a determination function 154, and a storage function 155 as processing functions of the processing circuitry 150.

The acquisition function 151 acquires pixel values of at least three different types of MR images. The at least three types of images may be obtained by imaging at least three times, or may be obtained by imaging twice or less. The display control function 152 causes the display 140 to display a diagram in which values based on the pixel values acquired by the acquisition function 151 are arranged in a region with at least three-dimensional axes. The values based on the pixel values may be the pixel values themselves acquired by the acquisition function 151, or may be values obtained by performing processing such as normalization on the pixel values acquired by the acquisition function 151. The acquisition function 151 is an example of the acquisition unit. The display control function 152 is an example of the display control unit. The display 140 is an example of the display.

The specifying function 153 specifies a group of the values in the diagram displayed by the display control function 152. The group is, for example, a set of a plurality of values specified by the operator. The group is, for example, a set of a plurality of values included in a predetermined circle in the displayed diagram. The group can also be referred to as, for example, a set of a plurality of values with a predetermined distance therebetween in the displayed diagram. The display control function 152 also causes the display 140 to further display information indicating a group of values specified by the specifying function 153. The specifying function 153 is an example of a specifying unit.

The determination function 154 determines whether locations corresponding to the group are normal or abnormal, on the basis of positions in the diagram of the group of the values specified by the specifying function 153. The storage function 155 stores the diagram including the group of the values specified by the specifying function 153 and the MR images in the storage 120 or the image storage apparatus 2 in a readable manner. The determination function 154 is an example of a determination unit. The storage function 155 is an example of a storage unit. The storage 120 and the image storage apparatus 2 is an example of a storage device.

The processing circuitry 150 is implemented by a processor, for example. In such a case, the processing functions of the processing circuitry 150 is stored in the storage 120 in the form of computer-executable programs, for example.

The processing circuitry 150 reads and executes the computer programs stored in the storage 120, thereby implementing functions corresponding to the computer programs. In other words, the processing circuitry 150 in the state of reading the computer programs has the processing functions illustrated in FIG. 1.

The following is a detailed description of an example of processing performed by each processing function of the processing circuitry 150 described above.

Figure 2:
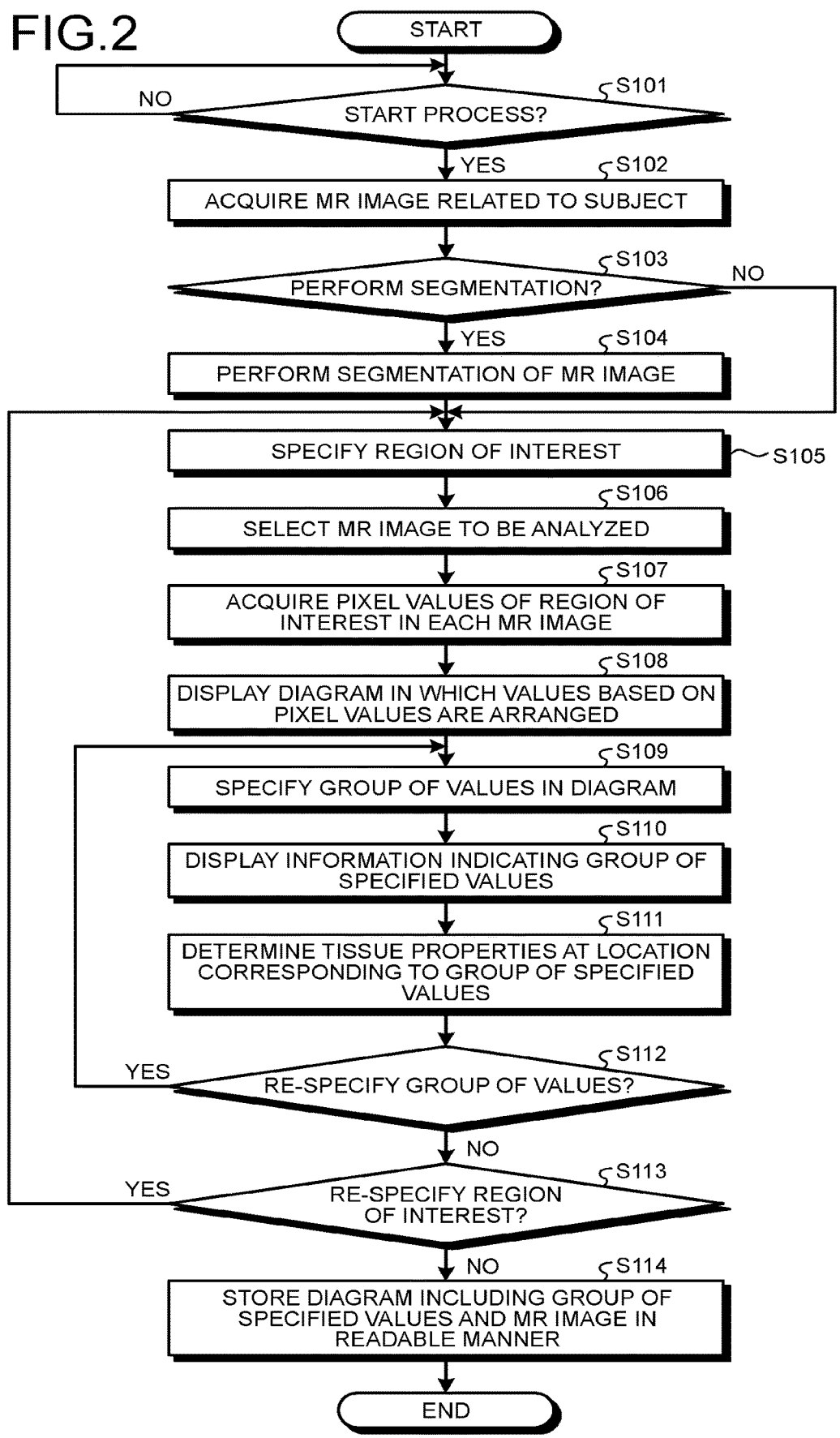
FIG. 2 is a flowchart illustrating an example of a processing procedure of processing performed by each processing function of processing circuitry according to the first embodiment.

FIG. 2 is a flowchart illustrating an example of a processing procedure of processing performed by each processing function of the processing circuitry 150 according to the first embodiment. FIG. 3 to FIG. 7 are diagrams illustrating an example of a processing result of processing performed by each processing function of the processing circuitry 150 according to the first embodiment.

For example, as illustrated in FIG. 2, first, the display control function 152 starts an analysis process according to an instruction from the operator (Yes at step S101 in FIG. 2).

Figure 3:
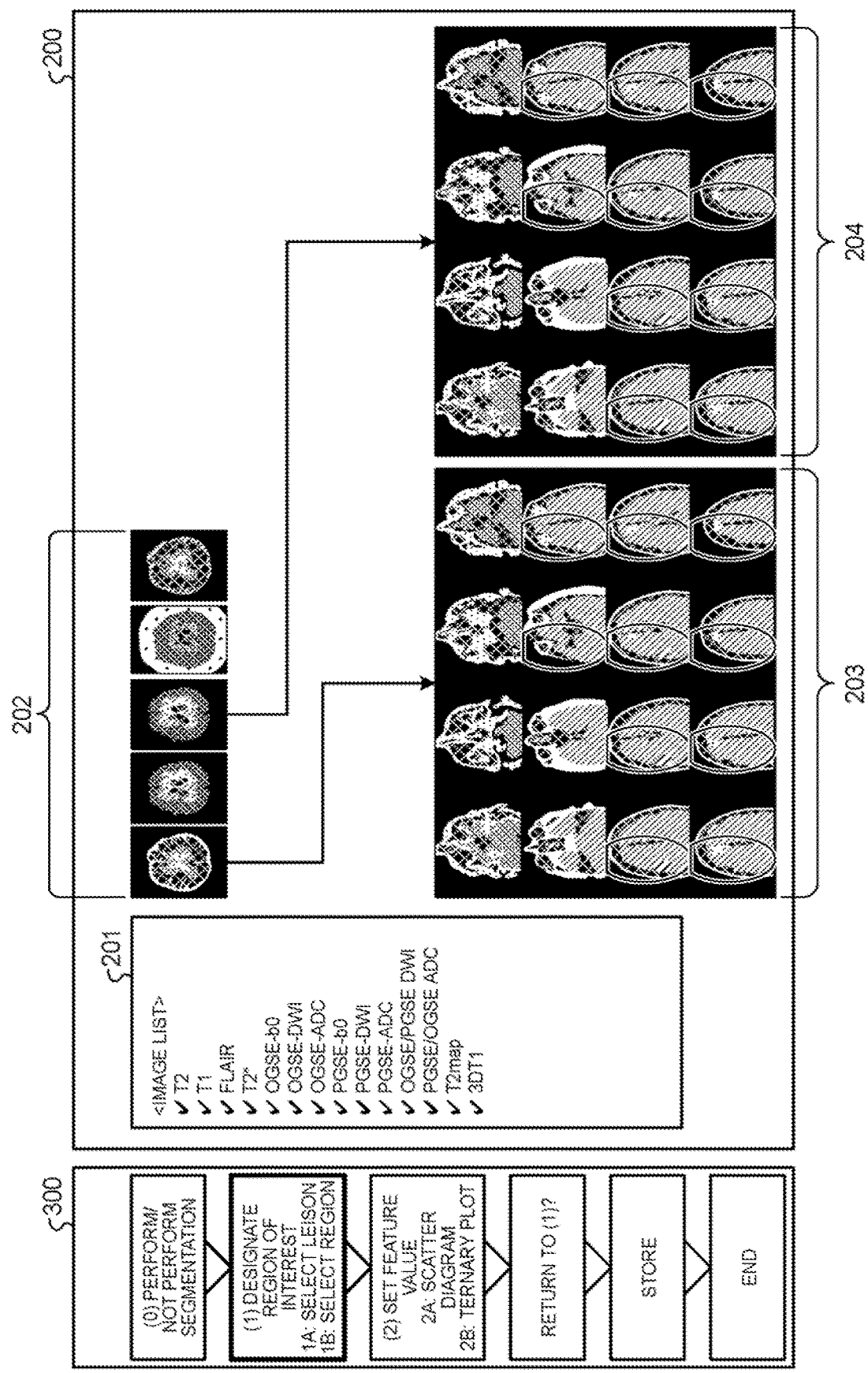
FIG. 3 is a diagram illustrating an example of a processing result of processing performed by each processing function of the processing circuitry according to the first embodiment.

For example, as illustrated in FIG. 3, the display control function 152 causes the display 140 to display an operation screen including a work region 200 for analysis and a progress status region 300 indicating the progress of the analysis process, according to an instruction from the operator.

Then, the acquisition function 151 acquires a plurality of MR images of a subject to be diagnosed, according to an instruction from the operator (step S102 in FIG. 2).

For example, the acquisition function 151 receives an operation of designating a subject to be diagnosed from the operator, and acquires MR images of the designated subject from the MRI apparatus 1 or the image storage apparatus 2. The MR images may be three-dimensional images (volume data) or a plurality of two-dimensional images (multi-slice data).

For example, the acquisition function 151 acquires, as the MR images, a T2 weighted (T2W) image, a T1 weighted (T1W) image, a fluid attenuated inversion recovery (FLAIR) image, a T2*weighted (T2*W) image, an oscillating gradient spin echo (OGSE)-b0 image, an OGSE-DW (diffusion weighted) image, an OGSE-ADC image, a pulsed gradient spin echo (PGSE)-b0 image, a PGSE-DW image, a PGSE-ADC (apparent diffusion coefficient) image, an OGSE/PGSE-DW image, a PGSE-ADC image, a T2 map image, and the like. The image types acquired by the acquisition function 151 are not limited to the above image types. The image type is not limited to the MR image, but may also be an image of another modality such as an X-ray CT apparatus.

For example, as illustrated in FIG. 3, the acquisition function 151 generates a list 201 of the plurality of acquired MR images and a reduced image 202 and causes the work region 200 to display the generated list 201 and reduced image 202 on the operation screen.

Subsequently, the acquisition function 151 receives, from the operator, an operation of designating whether to perform a segmentation of the acquired MR images (step S103 in FIG. 2).

When a designation to perform the segmentation is received (Yes at step S103 in FIG. 2), the acquisition function 151 performs the segmentation of the MR images by performing processing for fitting the acquired MR images into a standard model (step S104 in FIG. 2). The segmentation method can be any known method, and is not limited to the above example.

For example, when a site to be diagnosed is the brain, the acquisition function 151 performs segmentation using a standard model representing a plurality of anatomically or functionally divided regions of a standard brain, thereby dividing the brain region depicted in the MR image into a plurality of regions. Examples of the plurality of regions related to the brain include regions such as cortex (gray matter), white matter, frontal lobe, parietal lobe, temporal lobe, and occipital lobe, regions where blood is circulated by arteries of the anterior circulation system, regions where blood is circulated by arteries of the posterior circulation system, regions divided by Brodmann area, and the like.

On the other hand, when a designation not to perform the segmentation is received (No at step S103 in FIG. 2), the acquisition function 151 proceeds to the next step without performing the segmentation of the MR images.

Subsequently, the acquisition function 151 receives, from the operator, an operation of designating a region of interest with respect to one of the plurality of acquired MR images, and specifies a region of interest in other MR images on the basis of the designated region of interest (step S105 in FIG. 2).

For example, as illustrated in FIG. 3, the acquisition function 151 receives, from the operator, an operation of selecting one MR image from the plurality of MR images included in the list 201 or the reduced image 202 displayed on the operation screen. The acquisition function 151 causes the work region 200 to display a plurality of slice images 203 included in the MR image selected by the operator. Then, the acquisition function 151 receives, from the operator, an operation of designating a region of interest (oval-shaped region illustrated in FIG. 3) with respect to the plurality of displayed slice images 203, and specifies the region of interest in all MR images (for example, a plurality of slice images 204) including other unselected MR images, on the basis of the designated region of interest.

The number of regions of interest specified may be one or plural. For example, the acquisition function 151 receives, from the operator, an operation of designating, as a region of interest, a range including pathological conditions to be diagnosed (pathological conditions suspected in a subject to be diagnosed) with respect to the slice images 203. Alternatively, for example, the acquisition function 151 displays, on the slice images 203, information indicating the plurality of regions divided by the above-described segmentation, and receives, from the operator, an operation of designating one or more regions of interest from the plurality of regions.

Moreover, the acquisition function 151 receives, from the operator, an operation of selecting another MR image from the reduced image 202 of the plurality of MR images, and causes the work region 200 to display the plurality of slice images 204 included in the selected another MR image together with the region of interest. This makes it possible for the operator to check whether the region of interest is properly specified even in other MR images.

Subsequently, the acquisition function 151 selects at least three types of MR images from the plurality of MR images as MR images to be analyzed (step S106 in FIG. 2).

For example, the acquisition function 151 receives, from the operator, an operation of designating at least three types of MR images from the plurality of MR images included in the list 201 or the reduced image 202 displayed on the operation screen, and selects the designated MR images as MR images to be analyzed.

Alternatively, the acquisition function 151 may select MR images to be analyzed according to pathological conditions to be diagnosed. In such a case, for example, the storage 120 stores information indicating at least three types of MR images suitable for diagnosing each of a plurality of the pathological conditions. The acquisition function 151 receives, from the operator, an operation of designating pathological conditions to be diagnosed, specifies an MR image suitable for diagnosing the designated pathological conditions by referring to the information stored in the storage 120, and selects the MR image as an MR image to be analyzed. The acquisition function 151 may also acquire the pathological conditions to be diagnosed from an electronic medical record system or the like.

Figure 4:
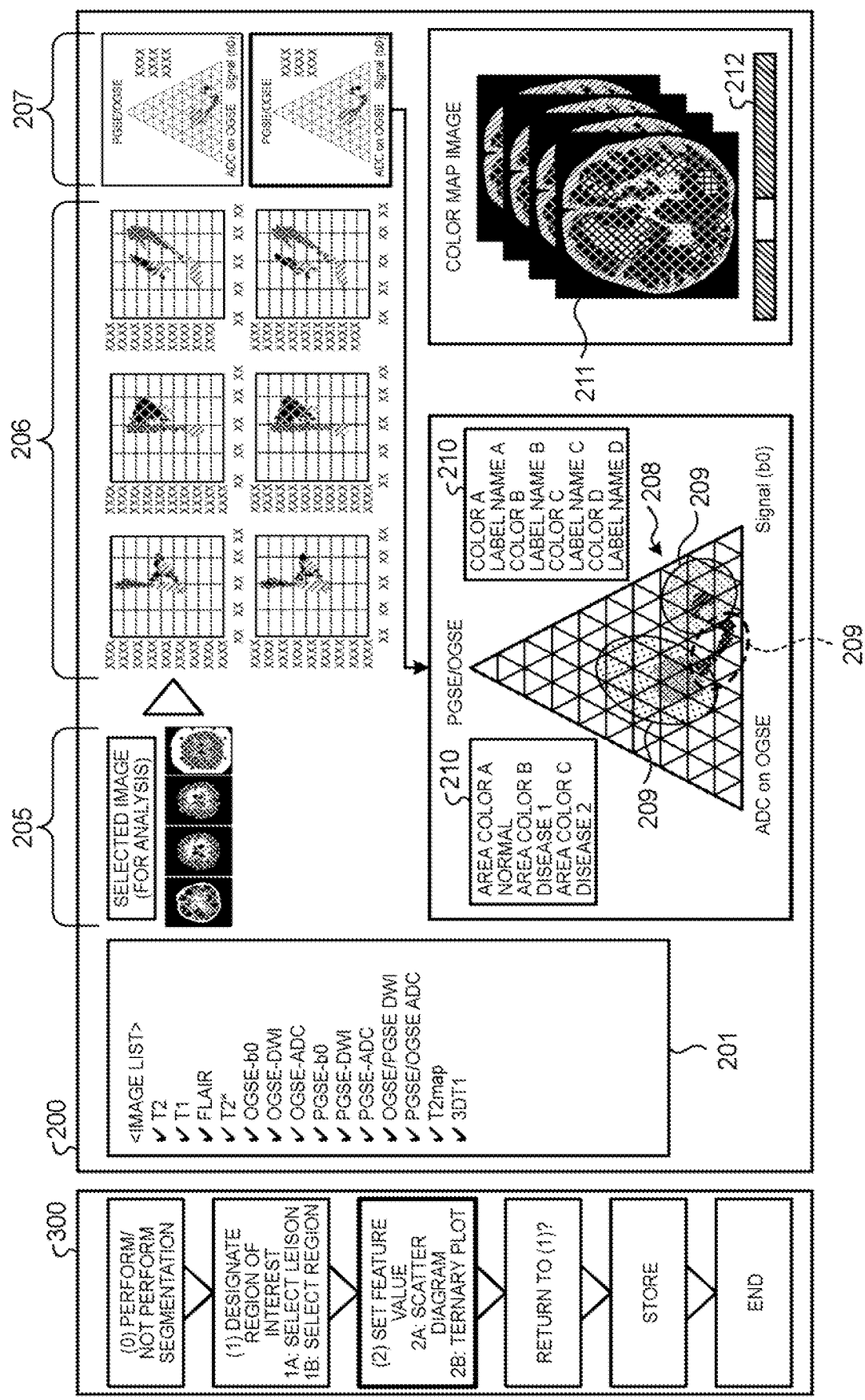
FIG. 4 is a diagram illustrating an example of a processing result of processing performed by each processing function of the processing circuitry according to the first embodiment.

For example, as illustrated in FIG. 4, the acquisition function 151 generates a reduced image 205 of the selected MR image to be analyzed and causes the work region 200 to display the reduced image 205 on the operation screen.

Subsequently, the acquisition function 151 acquires pixel values of the region of interest in each MR image with respect to the MR image to be analyzed (step S107 in FIG. 2).

Then, the display control function 152 causes the display 140 to display a diagram in which values based on the pixel values acquired by the acquisition function 151 are arranged in a region with at least three-dimensional axes (step S108 in FIG. 2).

For example, the display control function 152 causes the display 140 to display a scatter diagram and a ternary plot as the diagram in which the values based on the pixel values are arranged. The scatter diagram is a diagram in which values related to two types of MR images are arranged in a region with two-dimensional axes. The ternary plot is a diagram in which composition ratios of values related to three types of MR images are arranged in a triangular region with three-dimensional axes.

For example, as illustrated in FIG. 4, the display control function 152 generates a plurality of scatter diagrams 206 by using two MR images each to be analyzed, and causes the work region 200 to display the plurality of generated scatter diagrams 206 on the operation screen. The display control function 152 also generates a plurality of ternary plots 207 by using three MR images each to be analyzed, and causes the work region 200 to display the plurality of generated ternary plots 207 on the operation screen.

In such a case, for example, when the number of types of MR images to be analyzed is greater than the number of dimensions of the diagram, the display control function 152 determines at least one combination of MR images with the same number as the number of dimensions of the diagram among the MR images.

The number of combinations of the MR images to be determined may be one or plural. That is, the number of diagrams to be displayed on the operation screen may be one or plural. The number of types of diagrams to be displayed may be one or plural. For example, the number of combinations of the MR images, the number of diagrams to be displayed, and the types of diagrams to be displayed may be determined in advance for each pathological condition to be diagnosed and each type of diagram, or may be designated by the operator. All diagrams that can be produced from the MR images selected for analysis may be generated and displayed.

For example, the display control function 152 determines the combination of the MR images on the basis of the pixel values of the MR images to be analyzed. Specifically, the display control function 152 determines the combination of the MR images on the basis of pixel values within the region of interest. This takes advantage of differences in the distribution of pixel values according to tissues. In this case, for example, the storage 120 stores, for each pixel value, information indicating the combination of the MR images suitable for diagnosing each region of interest. Then, the display control function 152 refers to the information stored in the storage 120, and determines, on the basis of the pixel values of the MR image acquired by the acquisition function 151, the combination of MR images suitable for diagnosing a tissue indicated by the pixel values.

For example, on the basis of a position of the region of interest specified by the acquisition function 151, the display control function 152 determines the combination of the MR images. In this case, for example, the storage 120 stores, for each position of the region of interest, information indicating the combination of the MR images suitable for diagnosing each region of interest. Then, the display control function 152 refers to the information stored in the storage 120, and determines, on the basis of the position of the region of interest specified by the acquisition function 151, the combination of the MR images suitable for diagnosing the region of interest. This makes it possible to display a diagram suitable for diagnosing the region of interest according to the position of the region of interest. When a tissue of a site or the like can be recognized by segmentation, the position of the region of interest indicates the site. That is, it can be said that the display control function 152 determines the combination of the MR images on the basis of the site indicated by the position of the region of interest specified by the acquisition function 151. In this case, for example, the storage 120 stores, for each site, information indicating the combination of the MR images suitable for diagnosing each region of interest.

For example, the display control function 152 determines the combination of the MR images so that the group of the values is specifiable in the diagram in which the values based on the pixel values are arranged. In this case, for example, the storage 120 stores, for each type of diagram, information indicating the combination of MR images in which the group of the values is specifiable for each of a plurality of pathological conditions. Then, the display control function 152 refers to the information stored in the storage 120, and determines the combination of the MR images, in which the group of the values is specifiable, according to pathological conditions to be diagnosed. This can improve the accuracy of specifying the group of the values, which is performed by the specifying function 153 to be described below.

Then, the display control function 152 causes the display 140 to display the diagram, in which the values based on the pixel values are arranged, regarding at least one determined combination.

In this case, for example, the display control function 152 normalizes at least one of the axes of the diagram and causes the display 140 to display the diagram by using the normalized axis. For example, the display control function 152 determines, for each MR image, the range of pixel values in which the contrast of the pathological condition to be diagnosed is clearly expressed, and normalizes the axes constituting the diagram by assigning the determined range of the pixel values to an axis corresponding to each MR image. This makes it possible to more effectively display the diagram so that the distribution of values based on the pixel values is shown in a will-balanced manner on the diagram. The normalization process may be omitted.

For example, when a plurality of regions of interest are specified by the acquisition function 151, the display control function 152 superimposes values based on pixel values acquired from each region of interest in one diagram so that the values are displayed. Alternatively, for example, when a plurality of regions of interest are specified by the acquisition function 151, the display control function 152 may arrange values based on pixel values acquired from each region of interest in separate diagrams for each region of interest so that the values are displayed.

For example, as illustrated in FIG. 4, when an operation of designating one of the plurality of scatter diagrams 206 or the plurality of ternary plots 207 displayed on the operation screen is received from the operator, the display control function 152 enlarges the designated diagram and causes the work region 200 to displays the enlarged diagram.

For example, the display control function 152 causes the display 140 to display a ternary plot 208 in which composition ratios of pixel values of the OGSE-ADC image, the PGSE/OGSE-ADC image, and the DW image (b=0) are arranged.

Then, on the basis of the pixel values acquired by the acquisition function 151, the specifying function 153 specifies a group of values in the diagram displayed by the display control function 152 (step S109 in FIG. 2).

For example, as illustrated in FIG. 4, the specifying function 153 receives, from the operator, an operation of designating a range 209 of any size including the group of the values on the ternary plot 208 enlarged and displayed on the operation screen, and specifies the group of the values in the ternary plot 208. The specifying function 153 also receives, from the operator, an operation of assigning any color to the designated range 209. Moreover, the specifying function 153 receives, from the operator, an operation of correlating an arbitrary label name to the color assigned to the designated range 209. The specifying function 153 may also automatically specify the group of the values in the ternary plot 208. For example, the specifying function 153 may specify, as a group, a set of a plurality of values with a distance equal to or less than a predetermined value therebetween in the ternary plot 208. The specifying function 153 may automatically assign a color to the specified group. The specifying function 153 may also receive, from the operator, an operation of changing the automatically specified group and the color assigned to the group.

The number of ranges 209 to be designated may be one or plural. For example, when a plurality of ranges 209 are designated, the specifying function 153 receives, from the operator, an operation of assigning different colors (color A, color B, color C, color D, or the like) to each range. In this case, for example, the specifying function 153 may receive an operation of assigning a similar color to the ranges 209 having similar properties. For example, the specifying function 153 receives, from the operator, an operation of correlating different label names (normal, disease 1, disease 2, label name A, label name B, label name C, label name D, or the like) to each color assigned to each range. For example, the range 209 and/or colors indicating normal, disease 1, disease 2, or the like in the ternary plot 208 may be stored in advance for combinations of the axes of the ternary plot. For example, a range 209 and/or colors produced in the past in the ternary plot 208 may be stored, and in this case, the past range 209 and/or colors with the same axis information may be displayed as a range 209 and/or colors in an initial state in a ternary plot 208. The specifying function 153 may also receive, from the operator, an operation of changing the range 209 and/or colors in the initial state.

For example, on the basis of the group of the values specified on the ternary plot 208, the specifying function 153 may further specify a group of corresponding values on another scatter diagram and ternary plot.

Then, the display control function 152 causes the display 140 to further display information indicating the group of the values specified by the specifying function 153 (step S110 in FIG. 2).

For example, as illustrated in FIG. 4, the display control function 152 displays a region, which indicates the range 209 designated by the operator, with a line indicating the outline of the region, on the ternary plot 208 displayed on the operation screen. The display control function 152 also displays the group of the values, which are included in the range 209 designated by the operator, with the color assigned to the range 209. The display control function 152 also causes information 210 indicating a label name correlated to each color to be displayed in the vicinity of the ternary plot 208. In FIG. 4, area colors A, B, and C shown in the information 210 on the left side indicate the colors of the ranges 209, for example. The colors A, B, C, and D shown in the information 210 on the right side indicate the colors of the values plotted on the ternary plot 208, for example.

For example, the display control function 152 causes the display 140 to display a diagram and an MR image so that positions corresponding to values included in the group specified by the specifying function 153 can be identified on the MR image.

For example, as illustrated in FIG. 4, the display control function 152 generates color map images 211, and causes the work region 200 to display the color map images 211 on the operation screen, each of the color map images 211 being an MR image in which pixels at positions corresponding to the group of the values specified on the ternary plot 208 are given the same color as the group among pixels included in the MR image. The MR image used for generating the color map image 211 may be any of the MR images used for generating the ternary plot 208, or another MR image.

For example, the display control function 152 generates the color map image 211 for each slice image by using a plurality of slice images included in the MR image, and switches and displays each color map image 211 according to an instruction from the operator. For example, the display control function 152 switches and displays each color map image 211 according to an operation of moving a slider of a slider bar 212 displayed together with the color map image 211.

For example, the display control function 152 may cause the display 140 to display the diagram and the MR image so that a position, other than the region of interest corresponding to the group of the values specified by the specifying function 153, can be further identified on the MR image.

For example, the display control function 152 displays pixels, which have the same pixel values as pixels corresponding to the group of the values specified on the ternary plot 208 among pixels included in a region other than the region of interest, on the color map image 211 by using the same color as the group. The display control function 152 may cause the display 140 to display pixels in the region of interest and pixels outside the region of interest to be identifiable on the color map image 211 among the pixels having the same pixel values as the pixels corresponding to the group of the values specified on the ternary plot 208. For example, the display control function 152 may cause the display 140 to display the pixels to be identifiable by making one display form, such as transparency or blinking state, different from the other display form.

Figure 5:
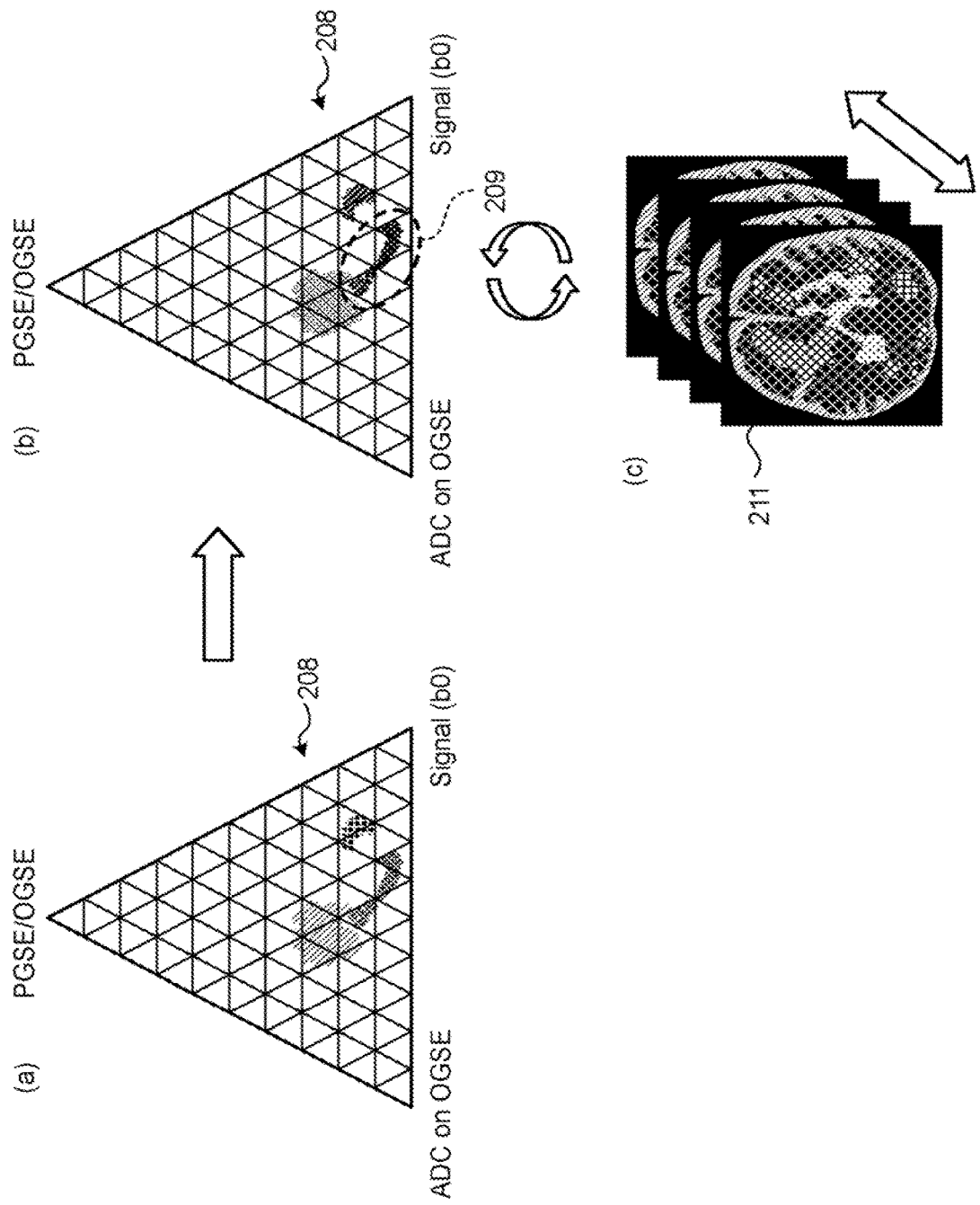
FIG. 5 is a diagram illustrating an example of a processing result of processing performed by each processing function of the processing circuitry according to the first embodiment.

In this way, in the present embodiment, for example, as illustrated in (a) and (b) of FIG. 5, after the range 209 is designated by the operator on the ternary plot 208, the display control function 152 causes the group of values included in the range 209 to be displayed with the color assigned to the range 209.

For example, as illustrated in (c) of FIG. 5, the display control function 152 generates, for each slice image, the color map image 211 in which pixels at positions corresponding to the group of the values specified on the ternary plot 208 among the pixels included in the MR image are given the same color as the group, and causes the color map image 211 to be displayed.

According to these processes, by designating the range 209 including a group of characteristic values on the ternary plot 208, positions corresponding to the group are displayed with the same color on the color map image 211. This makes it possible to easily ascertain positions on the MR image to which the group of the characteristic values displayed on a ternary plot 208 corresponds. By switching and displaying the color map image 211 generated for each slice image, a corresponding position can be confirmed for each slice image.

Then, the determination function 154 determines tissue properties at a location corresponding to the group on the basis of the positions in the diagram of the group of the values specified by the specifying function 153 (step S111 in FIG. 2). For example, the determination function 154 may determine whether the tissue properties at the location corresponding to the group are normal or abnormal, or may determine the type of disease.

For example, the determination function 154 inputs a diagram including a group of specific values, and determines the tissue properties at the location corresponding to the specified group by using a learned model constructed to output the tissue properties at the location corresponding to the group. In this case, the learned model is generated in advance using a machine learning method such as deep learning and stored in the storage 120. Then, the determination function 154 determines the tissue properties at the location corresponding to the group by inputting a diagram including the group of the values specified by the specifying function 153 into the learned model and acquiring an output result accordingly. The input to the learned model is not limited to the diagram including the group of the specific values, but may be any information indicating the position of the group of the specific values in the diagram. The determination on the tissue properties at the location corresponding to the specified group is not limited to the determination using the learned model, but may also be a determination using a table in which the position of the group of the specific values is correlated to the tissue properties.

Then, when the acquisition function 151 receives, from the operator, an instruction to re-specify the group of the values in the diagram (Yes at step S112 in FIG. 2), the process returns to step S109. However, when the acquisition function 151 receives, from the operator, no instruction to re-specify the group of values in the diagram (No at step S112 in FIG. 2), the process proceeds to the next step. This enables a series of processes from step S109 to step S111 described above to be repeated according to an instruction from the operator.

Subsequently, when the acquisition function 151 receives, from the operator, an instruction to re-specify a region of interest in the MR image (Yes at step S113 in FIG. 2), the process returns to step S105. However, when the acquisition function 151 receives, from the operator, no instruction to re-specify the region of interest in the MR image (No at step S113 in FIG. 2), the process proceeds to the next step. This enables a series of processes from step S105 to step S112 described above to be repeated according to an instruction from the operator.

Then, the storage function 155 stores the diagram including the group of the values specified by the specifying function 153 and the MR image (may include a color map image) in the storage 120 or the image storage apparatus 2 in a readable manner (step S114 in FIG. 2). For example, the storage function 155 stores the diagram including the group of the values specified by the specifying function 153 in the storage 120 or the image storage apparatus 2 in correlation with the MR image (may include a color map image). The storage function 155 may also store the pixel values of a region of interest and the position information of the region of interest. Moreover, the storage function 155 may store the values and position information of the group specified by the specifying function 153. The storage function 155 may also store the MR images that are the source of the ternary plot 208 and the color map image 211. Moreover, the storage function 155 may store a screenshot of the screen illustrated in FIG. 4. The storage function 155 may also store DICOM tag information (for example, imaging conditions and comments) of the MR images that are the source of the ternary plot 208 and the color map image 211. Each image may be stored as a DICOM image. Each image may be stored in a format such as BMP or PNG.

Figure 6:
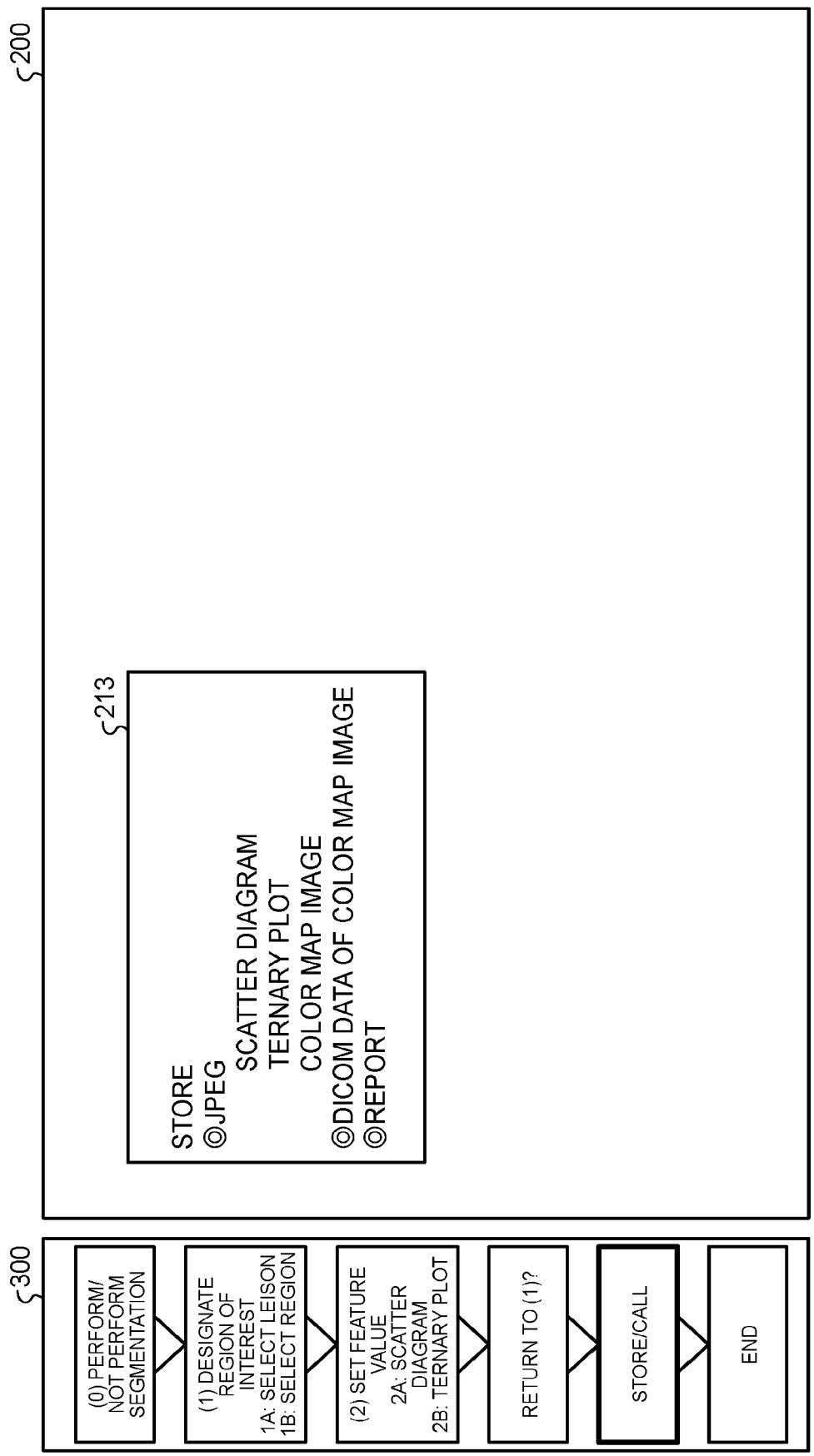
FIG. 6 is a diagram illustrating an example of a processing result of processing performed by each processing function of the processing circuitry according to the first embodiment.

For example, as illustrated in FIG. 6, the storage function 155 causes the work region 200 to display a menu 213 for designating data to be stored on the operation screen according to an instruction from the operator. Examples of the data to be stored include joint photographic experts group (JPEG) data for a scatter diagram, a ternary plot, and color map images, DICOM data for color map images, and reports. The storage function 155 stores data designated by the operator from the data included in the menu 213 displayed on the operation screen in the storage 120 or the image storage apparatus 2 in a readable manner.

For example, when the JPEG data for scatter and ternary plots is designated as the data to be stored, the storage function 155 generates and stores JPEG data for scatter and ternary plots in which the group of the specified values is colored. For example, when the JPEG data for color map images is designated as the data to be stored, the storage function 155 generates and stores JPEG data for color map images in which a position corresponding to the group of the specified values is colored.

For example, when the DICOM data for color map images is designated as the data to be stored, the storage function 155 generates and stores DICOM data for color map images in which a position corresponding to the group of the specified values is colored. For example, when the report is specified as the data to be stored, the storage function 155 generates and stores data for a report with key images being a scatter diagram, a ternary plot, and color map images colored in the same way as the JPEG data and the DICOM data.

In this case, for example, when storing each data, the storage function 155 receives, from the operator, an operation of designating a name for one data to be stored or a combination of a plurality of data to be stored, assigns the designated name, and stores each data or the combination of the data.

For example, the storage function 155 receives an operation of designating the name of a pathological condition from the operator, assigns the designated name of the pathological condition, and stores each data or the combination of the data.

Figure 7:
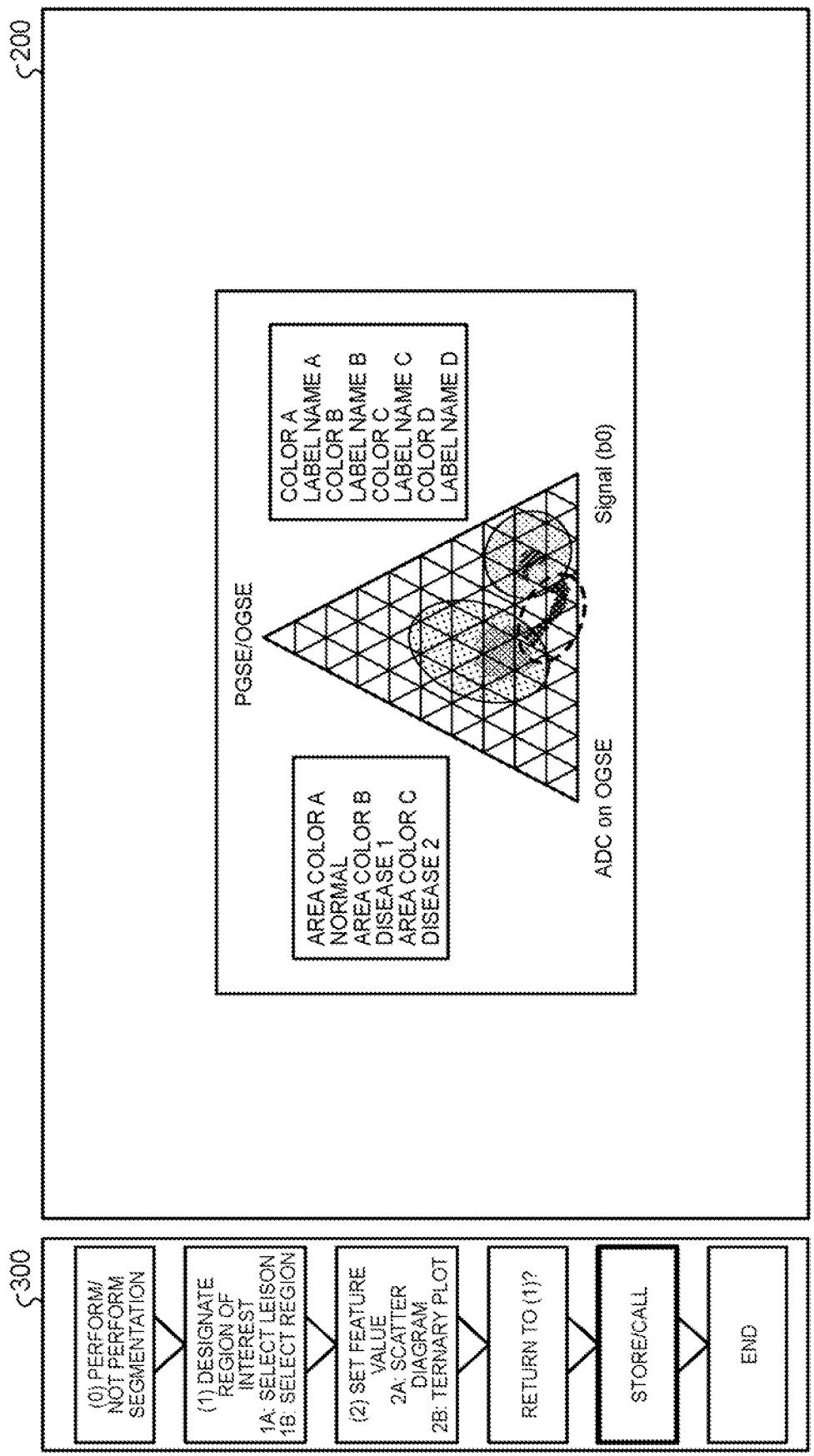
FIG. 7 is a diagram illustrating an example of a processing result of processing performed by each processing function of the processing circuitry according to the first embodiment.

For example, as illustrated in FIG. 7, the storage function 155 reads indicated data from the storage 120 or the image storage apparatus 2 according to an instruction from the operator, and displays the read data in the work region 200 on the operation screen. FIG. 7 illustrates an example in which a ternary plot is read and displayed in the work region 200 on the operation screen. An image read from the storage 120 or the image storage apparatus 2 and displayed in the work region 200 is not limited only to the ternary plot, but a ternary plot may be displayed together with at least one of a scatter diagram and an MR image (may include a color map image).

For example, the storage function 155 generates a list of names assigned to stored data and displays the list in the work region 200 on the operation screen according to an instruction from the operator, reads data designated by the operator from the displayed list, and displays the read data.

While the above-described processes are sequentially performed, the display control function 152 causes information indicating details of a process being performed to be displayed as needed in the progress status region 300 on the operation screen as illustrated in FIGS. 3, 4, 6 and 7, for example. This enables the operator to easily ascertain the progress status of an analysis process. For example, when it is not required to ascertain the progress status of the analysis process, the progress status region 300 does not necessarily have to be included in the operation screen.

The above is an example of the processing performed by each processing function of the processing circuitry 150. As described above, when the processing circuitry 150 is implemented by a processor, for example, the process of each step in FIG. 2 is implemented by the processing circuitry 150 that reads and executes a corresponding computer program from the storage 120.

For example, the processes of steps S101, S108 and S110 are implemented by the processing circuitry 150 that reads and executes a computer program corresponding to the display control function 152 from the storage 120. Furthermore, the processes of steps S102 to S107 and S112 and S113 are implemented by the processing circuitry 150 that reads and executes a computer program corresponding to the acquisition function 151 from the storage 120. Furthermore, the process of step S109 is implemented by the processing circuitry 150 that reads and executes a computer program corresponding to the specifying function 153 from the storage 120. Furthermore, the process of step S111 is implemented by the processing circuitry 150 that reads and executes a computer program corresponding to the determination function 154 from the storage 120. Furthermore, the process of step S114 is implemented by the processing circuitry 150 that reads and executes a computer program corresponding to the storage function 155 from the storage 120.

As describe above, in the first embodiment, the acquisition function 151 acquires pixel values of at least three different types of MR images. The display control function 152 causes the display 140 to display a diagram in which values based on the pixel values acquired by the acquisition function 151 are arranged in a region with at least three-dimensional axes.

According to the above configuration, diagnosis using MR images can be performed more easily. Particularly, when three types of MR images are used, it is possible to easily ascertain the three-dimensional distribution of the pixel values, that is, the state of tissue, by using a ternary plot. This is because the three-dimensional information is represented by one diagram, which makes it possible to reduce the amount of manipulation on the diagram by the operator.

For example, on the basis of pixel values of a plurality of types of MR images, it is possible to produce a diagram in which feature values of an interpretation target are arranged, and to clarify differences in tissue properties as a diagram. Furthermore, information obtained from the plurality of types of MR images can be integrated and shown on the diagram, allowing the operator to more intuitively understand differences in pathological conditions even without reconstructing the information obtained from the plurality of types of MR images.

For example, even in pathological conditions where the contrast itself is weak even after contrast enhancement, tissues with the same feature values can be highlighted, and differences in the pathological conditions can be clearly visualized. This makes it easier to ascertain the therapeutic effects of brain tumors and to distinguish between chronic and new lesions in multiple sclerosis (MS), for example. For example, in the treatment of brain tumors using Avastin as a therapeutic agent, the tumor may not be clearly imaged even when contrast-enhanced MR imaging is performed, but even in such a case, radiation necrosis and brain tumors can be more easily distinguished. This results in earlier diagnosis (understanding micro changes) of disease progression or therapeutic effects.

For example, by clearly showing differences in pathological conditions on the diagram, it is possible to reduce cases where it is difficult to make a decision in diagnosis, to reduce additional imaging, and to prevent an extension of examination time or increase a burden on a subject. Furthermore, even a person who is not an expert can easily make a diagnosis. Therefore, the above-described analysis process can be used not only by radiologists, but also as a tool for assisting each clinical doctor in interpreting images.

In the first embodiment, the specifying function 153 specifies a group of values in the diagram displayed by the display control function 152, on the basis of the pixel values acquired by the acquisition function 151. The display control function 152 causes the display 140 to further display information indicating the group of the values specified by the specifying function 153.

According to the above configuration, it is possible to more easily ascertain a group of characteristic values that may appear as differences.

For example, in the first embodiment, in order to identify positions on MR images corresponding to values included in the diagram in which the values based on the pixel values are arranged, the display control function 152 causes the display 140 to display the diagram and the MR images (color map images).

According to the above configuration, each group that appears as a difference can be displayed in association with a spatial position of an image, allowing the operator to easily ascertain the position of a tissue on the image.

For example, in the first embodiment, in order to further identify a position, other than a region of interest corresponding to the group of the values specified by the specifying function 153, on the MR image, the display control function 152 causes the display 140 to display the diagram and the MR image (color map image).

For example, in the diagram in which the values based on the pixel values are arranged, a characteristic distribution is shown depending on pathological conditions and tissue properties; however, according to the above configuration, tissues with the same feature values are displayed on the image, which makes it possible to prevent oversight even when the pathological conditions are outside a region of interest.

In the first embodiment, on the basis of the position in the diagram of the group of the values specified by the specifying function 153, the determination function 154 determines tissue properties at a location corresponding to the group.

According to the above configuration, it is possible to provide information for making a diagnosis more easily.

In the first embodiment, the storage function 155 stores the diagram including the group of the values specified by the specifying function 153 and the MR image in the storage 120 or the image storage apparatus 2 in a readable manner.

According to the above configuration, it is possible to make a diagnosis while comparing diagrams produced at different points in time and including the group of the values specified by the specifying function 153 and the MR images. For example, by assigning names of pathological conditions and storing diagrams, MR images, and color map images, it is possible to estimate pathological conditions on the basis of the distribution of values in the diagrams and the distribution of colors in the color map images.

Second Embodiment

The above-described first embodiment is an example of assigning a color to the designated range on the diagram in which the values based on the pixel values are arranged, but the embodiment is not limited to thereto. For example, before the range is designated on the diagram, the entire diagram may be assigned a plurality of colors that vary according to the value of each axis of the diagram.

Such an embodiment is described as a second embodiment. In the following embodiment, points different from the first embodiment are mainly described and detailed descriptions of points overlapping those already described are omitted.

FIG. 8 is a diagram illustrating an example of a processing result of processing performed by each processing function of the processing circuitry 150 according to the second embodiment In the present embodiment, for example, as illustrated in (a) of FIG. 8, when enlarging the ternary plot 208 designated by the operator and displaying the enlarged ternary plot 208 in the work region 200, the display control function 152 colors the ternary plot 208 in a plurality of colors that vary according to the value of each axis.

For example, as illustrated in (b) to (d) of FIG. 8, after the range 209 is designated by the operator on the pre-colored ternary plot 208, the display control function 152 generates the color map image 211 in which pixels at positions corresponding to the group of values included in the range 209 are assigned the same color as each value of the group, and causes the generated color map image 211 to be displayed.

According to these processes, as in the first embodiment, by designating the range 209 including a group of characteristic values on the ternary plot 208, positions corresponding to the group are displayed with the same color on the color map image 211. This makes it possible to easily ascertain positions on the MR image to which the group of the characteristic values displayed on the ternary plot 108 corresponds. By switching and displaying the color map image 211 generated for each slice image, a corresponding position can be confirmed for each slice image.

Consequently, according to the second embodiment, as in the first embodiment, diagnosis using MR images can be performed more easily. Moreover, according to the second embodiment, an operation of assigning a color to a specified range on the diagram is unnecessary, so that the analysis work can be performed more easily.

Modification

In the above-described embodiments, an example in which a scatter diagram and a ternary plot are used as the diagram in which the values based on the pixel values are arranged has been described; however, the embodiments are not limited thereto. For example, a radar chart may be used in which composition ratios of values related to three or more types of MR images are arranged in a polygonal region with three or more axes.

For example, in the above-described embodiments, an example in which the correspondence relationship between the group of the values specified on the drawing and positions on the MR image is indicated by color has been described; however, the embodiments are not limited thereto. For example, the correspondence relationship may be indicated by a design such as a pattern or a texture, instead of color. For example, when a plurality of groups of values are specified on the diagram, groups with similar properties may be colored in similar colors.

The analysis process described in the above embodiments may also be automatically performed as post-processing after MR images are taken. In such a case, for example, the storage 120 stores in advance, as setting information, conditions designated by the operator in the above-described embodiments. Then, each processing function refers to the setting information stored in the storage 120 and sequentially performs the processes, thereby continuously performing the series of processes described above.

Furthermore, in the above-described embodiments, an example in which the MR images are used has been described, but images used when producing the diagram in which the values based on the pixel values are arranged or color map images are not limited to the MR images. For example, medical images taken by a modality, such as an X-ray computed tomography (CT) apparatus, an ultrasonic diagnostic apparatus, an X-ray diagnostic apparatus, and a positron emission tomography (PET) apparatus, other than an MRI apparatus, may be used.

Other Embodiments

The configuration of the image processing apparatus 100 described in the above-described embodiments can also be applied to a system via a network such as a cloud. In such a case, for example, the same processing functions as the acquisition function 151, the display control function 152, the specifying function 153, the determination function 154, and the storage function 155 described above are implemented in processing circuitry provided in a server device included in the system. Then, the result of processing performed by each processing function implemented in the processing circuitry of the server device is transmitted to a client device used by a user of the system and displayed on a display or the like provided in the client device.

The configuration of the image processing apparatus 100 described in the above-described embodiments can also be applied to a console device of the MRI apparatus 1 and the image storage apparatus 2. In such a case, for example, the same processing functions as the acquisition function 151, the display control function 152, the specifying function 153, the determination function 154, and the storage function 155 described above are implemented in processing circuitry provided in the console device of the MRI apparatus 1 and the image storage apparatus 2.

Furthermore, in the above-described embodiments, the processing circuitry is not limited to those implemented by a single processor, but may be configured by combining a plurality of independent processors, and respective processors may implement respective processing functions by executing respective computer programs. Furthermore, the respective processing functions of the processing circuitry may be implemented by being appropriately distributed or integrated into single processing circuitry or a plurality of pieces of processing circuitry. Furthermore, the respective processing functions of the processing circuitry may be implemented by a combination of hardware such as circuits and software. Although an example in which the computer program corresponding to each processing function is stored in a single storage has been described, the embodiment is not limited thereto. For example, computer programs corresponding to the respective processing functions may be distributed and stored in a plurality of storages, and each processing circuitry may be configured to read each computer program from each storage and execute the read computer program.

In each of the above-described embodiments, an example in which the acquisition unit, the display control unit, the specifying unit, the determination unit, and the storage unit in this specification are implemented by the acquisition function 151, the display control function 152, the specifying function 153, the determination function 154, and the storage function 155 of the processing circuitry 150, respectively, has been described; however, the embodiments are not limited thereto. For example, the acquisition unit, the display control unit, the specifying unit, the determination unit, and the storage unit in this specification may be implemented by the acquisition function 151, the display control function 152, the specifying function 153, the determination function 154, and the storage function 155 described in the embodiments, or the same processing functions may also be implemented by hardware only, software only, or a combination of hardware and software.

Furthermore, the term "processor" used in the description of the aforementioned embodiment, for example, means a circuit such as a central processing unit (CPU), a graphics processing unit (GPU), an application specific integrated circuit (ASIC), or a programmable logic device (for example, a simple programmable logic device (SPLD), a complex programmable logic device (CPLD), and a field programmable gate array (FPGA)). Instead of storing the computer programs in the storage, the computer programs may be directly incorporated in the circuit of the processor. In this case, the processor implements the functions by reading and executing the computer programs incorporated in the circuit. Furthermore, each processor of the present embodiment is not limited to being configured as single piece of circuitry for each processor, and one processor may be configured by combining a plurality of pieces of independent circuitry to implement the functions thereof.

The computer program to be executed by the processor is provided by being incorporated in advance in a read only memory (ROM), a storage, and the like. The computer program may be provided by being recorded on a computer readable non-transitory storage medium, such as a CD (compact disc)-ROM, a flexible disk (FD), a CD-R (recordable), and a digital versatile disc (DVD), in a format installable or executable in these devices. Furthermore, the computer program may be provided or distributed by being stored on a computer connected to a network such as the Internet and downloaded via the network. For example, the computer program is configured as a module including the aforementioned each processing function. As actual hardware, the CPU reads and executes the computer program from the storage medium such as a ROM, so that each module is loaded on a main storage device and generated on the main storage device.

Furthermore, in the above-described embodiments, each component of each apparatus illustrated in the drawings is functionally conceptual, and does not necessarily have to be physically configured as illustrated in the drawings. That is, the specific form of dispersion or integration of each device is not limited to that illustrated in the drawings, but can be configured by functionally or physically dispersing or integrating all or part thereof in arbitrary units, depending on various loads and usage conditions. Moreover, each processing function performed by each device can be implemented in whole or in part by a CPU and a computer program that is analyzed and executed by the CPU, or by hardware using wired logic.

Of the processes described in the above embodiments, all or part of the processes described as being performed automatically can be performed manually, or all or part of the processes described as being performed manually can be performed automatically by known methods. Other information including processing procedures, control procedures, specific names, and various data and parameters shown in the above documents and drawings may be changed as desired, unless otherwise noted.

The various types of data handled herein are typically digital data.

According to at least one of the above-described embodiments, diagnosis using medical images can be performed more easily.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus, comprising:
processing circuitry configured to
acquire pixel values of at least three different types of magnetic resonance (MR) images;
cause a display to display a diagram in which values based on the pixel values are arranged in a region with at least three-dimensional axes, wherein
when a number of types of the MR images is greater than a number of dimensions of the diagram, the processing circuitry is further configured to determine at least one combination of MR images with a same number as the number of dimensions of the diagram among the MR images, and cause the display to display the diagram regarding the at least one combination, wherein
the processing circuitry is further configured to acquire pixel values of a region of interest in the MR images, and
the processing circuitry is further configured to determine the combination of the MR images based on a position of the region of interest.

2. The image processing apparatus according to claim 1, wherein the processing circuitry is further configured to cause the display to display a ternary plot as the diagram.

3. The image processing apparatus according to claim 2, wherein composition ratios of pixel values of an OGSE-ADC image, a PGSE/OGSE-ADC image, and a DW image are arranged in the ternary plot.

4. The image processing apparatus according to claim 1, wherein, when the number of types of the MR images is greater than the number of dimensions of the diagram, the processing circuitry is further configured to determine a plurality of combinations of MR images with the same number as the number of dimensions of the diagram among the MR images, and cause the display to display the diagram regarding the determined plurality of combinations.

5. The image processing apparatus according to claim 1, wherein the processing circuitry is further configured to normalize at least one of axes of the diagram, and cause the display to display the diagram by using the normalized axes.

6. The image processing apparatus according to claim 1, wherein, based on a region of interest designated by an operator with respect to one of the MR images, the processing circuitry is further configured to specify a region of interest in another MR image, and acquire pixel values of the region of interest in each MR image.

7. The image processing apparatus according to claim 1, wherein the MR images include at least three of a T2 weighted (T2W) image, a T1 weighted (T1W) image, a fluid attenuated inversion recovery (FLAIR) image, a T2*weighted (T2*W) image, an oscillating gradient spin echo (OGSE)-b0 image, an OGSE-DW (diffusion weighted) image, an OGSE-ADC image, a pulsed gradient spin echo (PGSE)-b0 image, a PGSE-DW image, a PGSE-ADC (apparent diffusion coefficient) image, an OGSE/PGSE-DW image, a PGSE/OGSE-ADC image, and a T2 map image.

8. The image processing apparatus according to claim 1, wherein the processing circuitry is further configured to acquire the pixel values after performing processing for fitting the MR images into a standard model.

9. The image processing apparatus according to claim 1, wherein the processing circuitry is further configured to cause the display to display a radar chart as the diagram.

10. The image processing apparatus according to claim 1, wherein
the processing circuitry is further configured to specify a group of the values in the diagram, and
the processing circuitry is further configured to cause the display to display information indicating the specified group of the values.

11. The image processing apparatus according to claim 10 wherein the processing circuitry is further configured to cause the display to display the diagram and the MR images so that positions corresponding to the values included in the group are identifiable on the MR images.

12. The image processing apparatus according to claim 10, wherein
the processing circuitry is further configured to acquire pixel values of a region of interest in the MR image, and
the processing circuitry is further configured to cause the display to display the diagram and the MR image so that a position, other than the region of interest corresponding to the specified group of the values, is identifiable on the MR image.

13. The image processing apparatus according to claim 10, wherein the processing circuitry is further configured to store the diagram including the specified group of the values and the MR image in a storage device in a readable manner.

14. The image processing apparatus according to claim 10, wherein, based on a position of the specified group of the values in the diagram, the processing circuitry is further configured to determine tissue properties at a location corresponding to the group.

15. A non-transitory computer-readable medium comprising a plurality of computer-executable instructions, wherein the plurality of instructions cause a computer to execute:
acquiring pixel values of at least three different types of magnetic resonance (MR) images;
causing a display to display a diagram in which values based on the pixel values are arranged in a region with at least three-dimensional axes, wherein
when a number of types of the MR images is greater than a number of dimensions of the diagram, the causing the display to display the diagram includes determining at least one combination of MR images with a same number as the number of dimensions of the diagram among the MR images, and causing the display to display the diagram regarding the at least one combination, wherein
the acquiring pixel values includes acquiring pixel values of a region of interest in the MR images, and
the causing the display to display the diagram includes determining the combination of the MR images based on a position of the region of interest.

16. An image processing apparatus, comprising:
processing circuitry configured to
acquire pixel values of at least three different types of medical images;
cause a display to display a diagram in which values based on the pixel values are arranged in a region with at least three-dimensional axes, wherein
when a number of types of the medical images is greater than a number of dimensions of the diagram, the processing circuitry is further configured to determine at least one combination of medical images with a same number as the number of dimensions of the diagram among the medical images, and cause the display to display the diagram regarding the at least one combination, wherein
the processing circuitry is further configured to acquire pixel values of a region of interest in the medical images, and
the processing circuitry is further configured to determine the combination of the medical images based on a position of the region of interest.

17. An image processing apparatus, comprising:
processing circuitry configured to
acquire pixel values of at least three different types of magnetic resonance (MR) images; and
cause a display to display a diagram in which values based on the pixel values are arranged in a region with at least three-dimensional axes, wherein,
when a number of types of the MR images is greater than a number of dimensions of the diagram, the processing circuitry is further configured to determine at least one combination of MR images with a same number as the number of dimensions of the diagram among the MR images, and cause the display to display the diagram regarding the at least one combination, wherein,
based on a region of interest designated by an operator with respect to one of the MR images, the processing circuitry is further configured to specify a region of interest in another MR image and acquire pixel values of the region of interest in each MR image, and based on a position of the region of interest, the processing circuitry is further configured to determine the combination of the MR images.

18. A non-transitory computer-readable medium comprising a plurality of computer-executable instructions, wherein the plurality of instructions cause a computer to execute:

acquiring pixel values of at least three different types of magnetic resonance (MR) images; and causing a display to display a diagram in which values based on the pixel values are arranged in a region with at least three-dimensional axes, wherein, when a number of types of the MR images is greater than a number of dimensions of the diagram, the causing the display to display the diagram includes determining at least one combination of MR images with a same number as the number of dimensions of the diagram among the MR images, and causing the display to display the diagram regarding the at least one combination, wherein, based on a region of interest designated by an operator with respect to one of the MR images, the acquiring pixel values includes specifying a region of interest in another MR image and acquiring pixel values of the region of interest in each MR image, and based on a position of the region of interest, the causing the display to display the diagram includes determining the combination of the MR images.

19. An image processing apparatus comprising:
processing circuitry configured to
acquire pixel values of at least three different types of medical images; and
cause a display to display a diagram in which values based on the pixel values are arranged in a region with at least three-dimensional axes, wherein,
when a number of types of the medical images is greater than a number of dimensions of the diagram, the processing circuitry is further configured to determine at least one combination of medical images with a same number as the number of dimensions of the diagram among the medical images, and cause the display to display the diagram regarding the at least one combination, wherein,
based on a region of interest designated by an operator with respect to one of the medical images, the processing circuitry is further configured to specify a region of interest in another medical image and acquire pixel values of the region of interest in each medical image, and
based on a position of the region of interest, the processing circuitry is further configured to determine the combination of the medical images.

* * * * *